United States Patent
Paul et al.

(10) Patent No.: US 6,833,068 B2
(45) Date of Patent: Dec. 21, 2004

(54) PASSIVE INJECTION CONTROL FOR MICROFLUIDIC SYSTEMS

(75) Inventors: Phillip H. Paul, Livermore, CA (US); Don W. Arnold, Livermore, CA (US); David W. Neyer, Castro Valley, CA (US)

(73) Assignee: Sandia National Laboratories, Livermore, CA (US)

( * ) Notice: Subject to any disclaimer, the term of this patent is extended or adjusted under 35 U.S.C. 154(b) by 129 days.

(21) Appl. No.: 10/341,870

(22) Filed: Jan. 13, 2003

(65) Prior Publication Data

US 2004/0134845 A1 Jul. 15, 2004

(51) Int. Cl.$^7$ ............................................. B01D 15/08
(52) U.S. Cl. ................... 210/198.2; 210/656; 204/601; 422/70
(58) Field of Search ................. 204/600, 601, 204/602, 603, 604, 605, 451, 452, 453, 454, 455, 450; 210/635, 656, 659, 198.2; 422/70

(56) References Cited

U.S. PATENT DOCUMENTS

| | | | | |
|---|---|---|---|---|
| 5,833,826 A | * | 11/1998 | Nordman | ................... 204/452 |
| 5,858,187 A | * | 1/1999 | Ramsey et al. | ............. 204/452 |
| 5,858,195 A | * | 1/1999 | Ramsey | ...................... 204/601 |
| 5,885,470 A | * | 3/1999 | Parce et al. | ................... 216/33 |
| 6,001,229 A | * | 12/1999 | Ramsey | ...................... 204/451 |
| 6,033,546 A | * | 3/2000 | Ramsey | ...................... 204/603 |
| 6,290,909 B1 | * | 9/2001 | Paul et al. | .................... 422/70 |
| 6,627,076 B2 | * | 9/2003 | Griffiths | ................. 210/198.2 |
| 6,752,922 B2 | * | 6/2004 | Huang et al. | ............ 210/198.2 |
| 2004/0031686 A1 | * | 2/2004 | Foret et al. | ................. 204/548 |

FOREIGN PATENT DOCUMENTS

| | | | | |
|---|---|---|---|---|
| WO | WO 96/04547 | 2/1996 | ............. 210/198.2 |

* cited by examiner

*Primary Examiner*—Ernest G. Therkorn
(74) *Attorney, Agent, or Firm*—Donald A. Nissen

(57) ABSTRACT

Apparatus for eliminating siphoning, "dead" regions, and fluid concentration gradients in microscale analytical devices. In its most basic embodiment, the present invention affords passive injection control for both electric field-driven and pressure-driven systems by providing additional fluid flow channels or auxiliary channels disposed on either side of a sample separation column. The auxiliary channels are sized such that volumetric fluid flow rate through these channels, while sufficient to move the sample away from the sample injection region in a timely fashion, is less than that through the sample separation channel or chromatograph.

20 Claims, 4 Drawing Sheets

US 6,833,068 B2

PASSIVE INJECTION CONTROL FOR MICROFLUIDIC SYSTEMS

STATEMENT OF GOVERNMENT INTEREST

This invention was made with Government support under contract no. DE-AC04-94AL85000 awarded by the U.S. Department of Energy to Sandia Corporation. The Government has certain rights in the invention.

CROSS-REFERENCE TO RELATED APPLICATIONS

Not applicable.

BACKGROUND OF THE INVENTION

This invention is directed to a novel configuration of fluid flow channels that provides for passive control of sample transport in microfluidic systems and particularly for controlling sample injection for miniature total analysis systems ($\mu$TAS). The apparatus and method disclosed herein can be used to control sample transport in systems that employ electrophoretic, electrochromatographic, and pressure-driven flow.

Recent advances in miniaturization have led to the development of microfluidic systems that are designed, in part, to perform a multitude of chemical and physical processes on a micro-scale. Typical applications include analytical and medical instrumentation, and industrial process control equipment. In this context, there is a need for devices to provide very precise control over small flows as well as small volumes of liquid in microscale channels. A common method for introducing a sample for analysis into a microscale separation channel is by means of voltage switching at the intersection of two intersecting channels. This method is illustrated generally in FIG. 1. There are essentially two steps involved in a typical sample injection. In the first step (FIG. 1A), a voltage is applied along channel 110 to move a sample through the channel (sample introduction channel). In step two (FIG. 1B), a voltage is applied along channel 120, the separation channel. When the voltage is switched from channel 110 to channel 120 that portion of the sample occupying the intersection between the two channels is carried into the separation channel 120 for subsequent analysis. Ideally, the process of switching voltage between channels serves to inject a precise and reproducible quantity of sample into the separation channel. However, in practice such is often not the case.

Electroosmotic-driven fluid flow, such as discussed above, is a 'potential flow' which means that fluid flow follows the paths traced by the streamlines of the electric field. Leakage occurs in this injection scheme because fluid streamlines, which correspond to electric field lines in electroosmotic-driven flow, enter the electrically floating channel. This phenomenon is graphically illustrated in FIG. 2 which shows the electric field lines at the intersection between channel 110 having an electric field contained therein and one that is floating 120. It can be seen that the electric field lines intrude a significant distance into the floating channel. This intrusion of electric field lines into the electrically floating channel not only explains the "leakage" shown in FIG. 3 but also explains why the sample fluid is observed to enter microchannel 120 prior to application of a potential gradient to that microchannel and fluid continues to flow (leak) into microchannel 120 after the potential gradient has ceased to be applied. As can be readily appreciated, these processes can introduce additional and unknown quantities of sample into the separation channel, thereby causing the analysis to be inaccurate.

The problem of leakage in injection devices has been recognized and means for mitigating this problem have been proposed. Ramsey in U.S. Pat. No. 5,858,195 and Published PCT Application No. WO96/04547 and Parce in U.S. Pat. No. 5,885,470 employed a scheme called "controlled electrokinetic material transport", to control cross-channel leakage in microchannel systems and particularly in arrangements of integrated microchannels. In this scheme separate electric potentials are applied across the various microchannels. However, these methods require careful control of multiple electrical power sources as well as a priori knowledge of the conductive properties of all fluids in all channels to determine the required voltages. Furthermore the method is susceptible to disruption due to variations in fluid compositions, hydrostatic pressure-driven interferences, and diffusion effects, all of which may degrade the quality or purity of the injected sample. Moreover, for each change in channel system design it is necessary to reconfigure, and perhaps refabricate, the electronics system to accommodate the design change. This is true even for changes that may not necessarily affect the general channel configuration and geometry but that change the electrochemical properties of the system, such as the conductivity or zeta potential. Moreover, this approach introduces a significant additional drain on the power supply.

Another approach to the problem of sample injection leakage has been described by Hasselbrink in U.S. patent application Ser. No. 09/669,862 "Method and Apparatus for Controlling Cross Contamination of Microfluid Channels", assigned to the same assignee and incorporated herein by reference in its entirety. Hasselbrink provides method and apparatus for reducing or substantially eliminating channel cross-contamination, due to electric field streamlines entering the floating channel, hydrostatic pressure effects, and mass diffusion, during microfluidic sample injections by a reduction of the cross-sectional area of the fluid flow channels in proximity to the intersection. A non-orthogonal intersection microchannel geometry can also be used in conjunction with reduction in cross-sectional area to reduce the leakage of electric field lines away from the intersection during sample injection. However, this approach suffers from the need for more complex channel fabrication.

It can be desirable to provide for parallel separations schemes on a given sample. In this way, several different analyses can be performed simultaneously on the same sample by proper configuration of the separation channels. As before, a portion of the sample to be analyzed can be introduced into each of a plurality of parallel separation channels by switching the sample-driving voltage to carry the portion into each separation channel. However, with this approach two significant problems arise. Referring now to FIG. 4, a volume of sample can be trapped in the region 310 between the individual separation channels 120. Unlike the case for a single separation channel (cf. FIG. 2), application of reduced voltages along the sample channel 110 cannot sweep the sample from the interchannel region. However, as before, electrical field line penetration into the sample channel allows a continuous sample flow into the separation channel by diffusion.

Because the different separation channels provide for different analyses, the buffer solutions that flow in the different channels can have different compositions and thus different electrical conductivities, pH, compositions, etc. If the solutions from the different separation channels are allowed to mix the desirable plug-like flow associated with electrokinetic fluid pumping mechanism can be compromised degrading the separation performance of the device.

Prior art sample schemes for the injection of a sample volume into a separation channel have been illustrated by the application of an electric field to the separation channel. However, sample injection can also be accomplished by the application of a pressure. While the issue of sample leakage onto a single sample channel is not as critical for pressure injection as for electroosmotic flow injection schemes, problems with parallel channel separations discussed above remain.

SUMMARY OF THE INVENTION

Accordingly, the present invention is directed to apparatus and method for eliminating the undesirable effects of siphoning, "dead" regions, and concentration gradients that are present in conventional microfluidic analytic devices by providing strategically placed fluid flow channels, or auxiliary channels, whose purpose is to provide alternate routes for sample transport that can be toward or away from channel intersections, i.e., passive injection control.

As discussed above, problems with injecting a sample from a sample channel to a separation channel in an electric field-driven microfluidic system are due, principally, to lack of control of electric field lines, i.e., propagation of electric field lines into regions where they produce deleterious effects. Prior means of control involved, inter alia, the use of multiple power supplies or complicated electronics to define the electric field at all points in a microfluidic system.

In its most basic embodiment, the present invention affords passive injection control of sample transport for both electric field-driven and pressure-driven systems by providing additional fluid flow channels or auxiliary channels disposed on either side of a sample separation column. The inlet ends of these auxiliary flow channels can be joined conveniently with the inlet end of the sample separation column proximate the point of sample injection. Similarly, the outlet ends of the side channels can be joined conveniently with the outlet end of the sample separation channel. The auxiliary flow channels are sized such that volumetric fluid flow rate through these channels, while sufficient to move the sample away from the sample injection region in a timely fashion, is less than that through the separation channel. In general, it is preferred that the ratio of fluid flow rate through the separation channel to that through the auxiliary channels be on the order of about 10:1. It will be appreciated that since channel volume is a product of the channel cross-sectional area and channel length, fluid flow through a channel can be affected by changes in either of these parameters s well as by packing the auxiliary flow channels with a packing material to reduce the fluid flow rate through these channels.

BRIEF DESCRIPTION OF THE DRAWINGS

The accompanying drawings, which are incorporated in and form part of the specification, illustrate the present invention and, together with the description, explain the invention. In the drawings like elements are referred to by like numbers.

DETAILED DESCRIPTION OF THE INVENTION

Figures 1A, 1B:
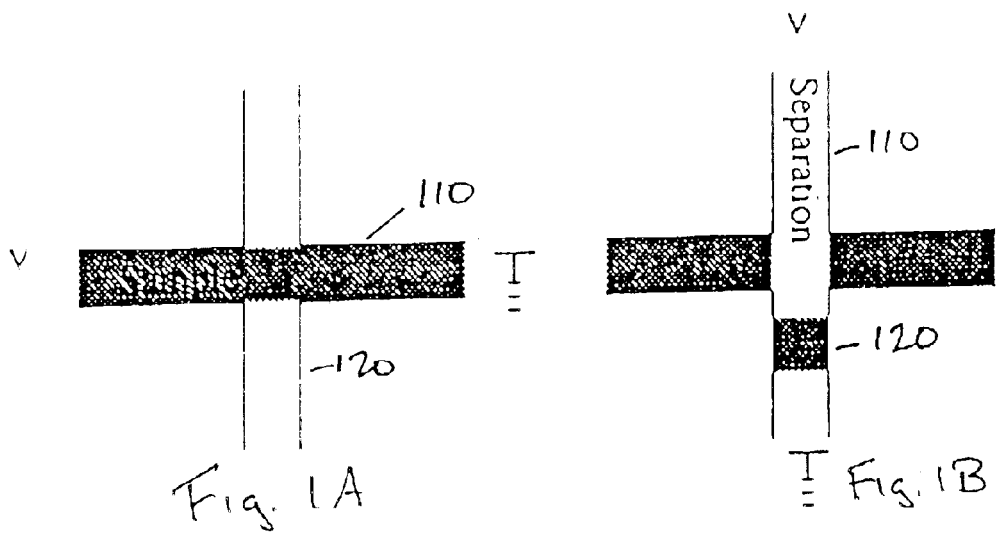
FIGS. 1A and 1B show a prior art sample injection configuration.
Figure 2:
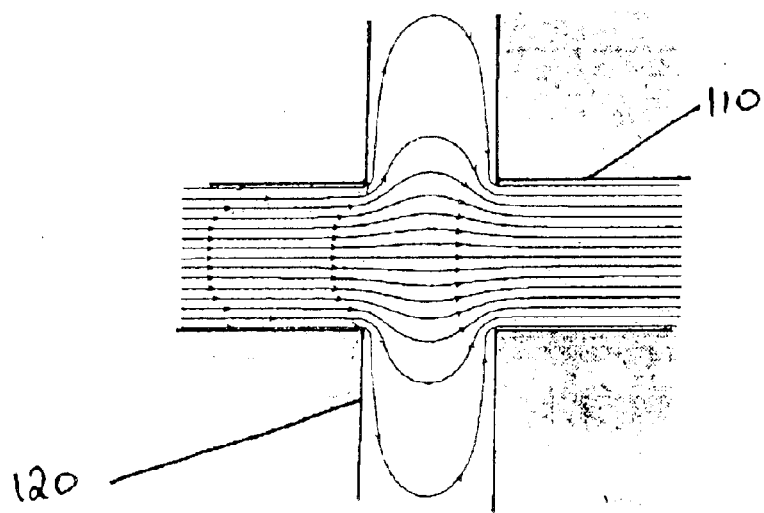
FIG. 2 illustrates electrical field line penetration into a prior art separation channel.
Figure 3:
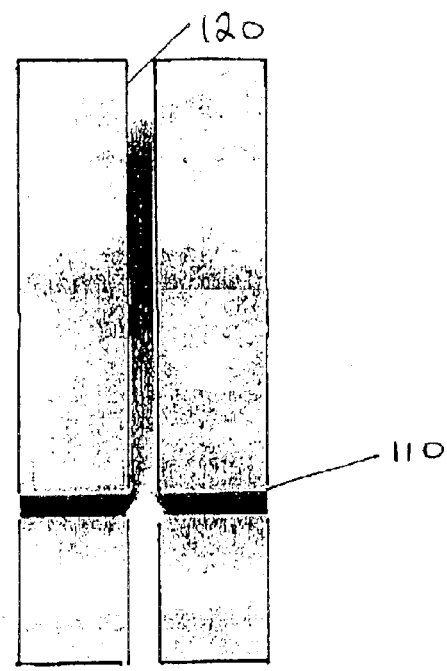
FIG. 3 shows sample leakage in a prior art configuration.
Figure 4:
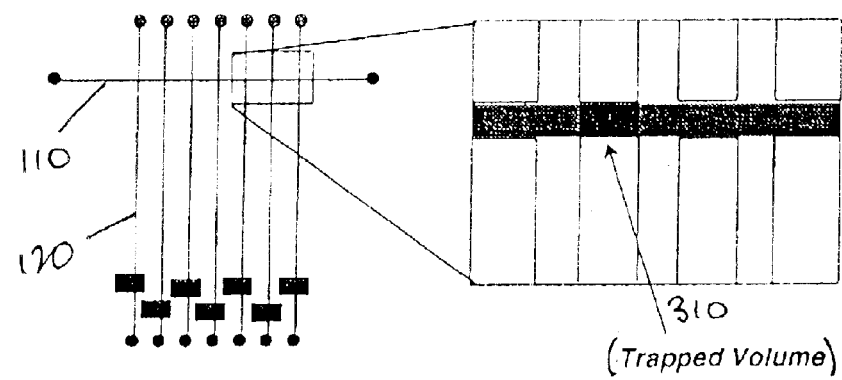
FIG. 4 shows a prior art multi-column arrangement.
Figure 5:
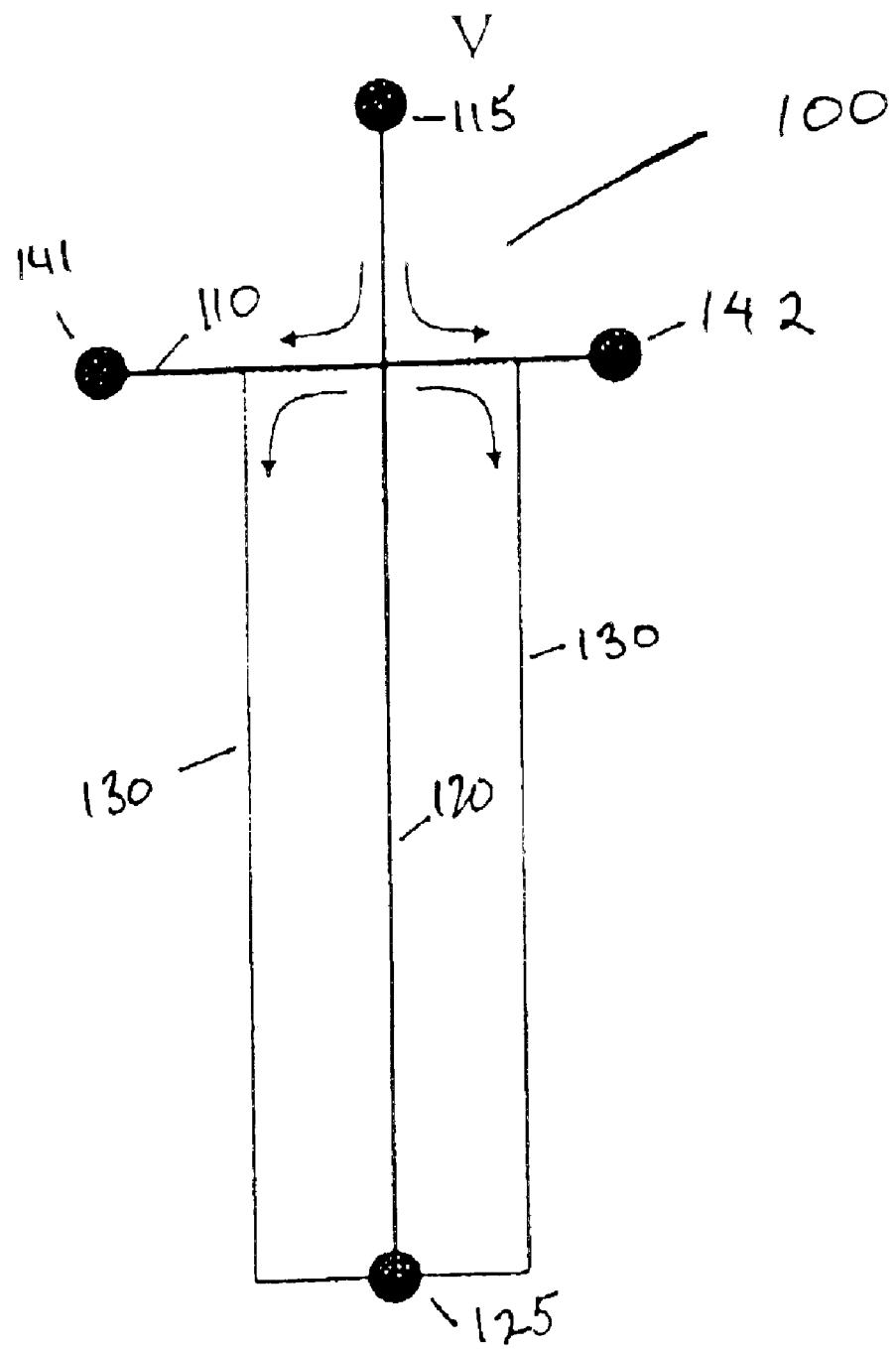
FIG. 5 is a schematic illustration of an embodiment of the invention.

The concept of the present invention is illustrated and exemplified by reference to FIG. 5. The microfluidic system 100 can be disposed on a substrate (not shown) and comprises a separation channel 120, an intersecting sample channel 110, a first reservoir 115 in fluid communication with the inlet of separation channel 120, and a second reservoir 125 in fluid communication with the outlet of the separation channel. Auxiliary flow channels 130 provide for passive fluid control and are disposed on either side of and proximate separation channel 120. Auxiliary channels 130 and 135 are preferably spaced equidistant from separation channel 120 and most preferably spaced from the separation channel a distance of about 5 to 10 hydraulic diameters of intersecting sample channel 110. As is well known by those skilled in the hydraulic art, the hydraulic diameter is defined as four times the cross-sectional area divided by the wetted perimeter. Thus, for a circle the hydraulic diameter is simply the diameter of the circle. For a rectangular pipe having dimensions of "w" by "h" the hydraulic diameter is 4 wh/(2 w+2 h).

The inlet ends of the auxiliary channels are in fluid communication with and desirably joined to sample channel 110 and the outlet ends of these auxiliary channels can be joined to separation channel 120 or second reservoir 125. Sample channel 110 is provided with a first reservoir 141 in fluid communication with the inlet of sample channel 140, and a second reservoir 142 in fluid communication with the outlet of the separation channel. Referring now to FIG. 5, it can be seen that reservoirs 115 and 125 associated with separation channel 120 are separate and distinct from reservoirs 141 and 142 associated with sample channel 110. It is understood throughout the written description of the invention that all the channels are covered or enclosed unless explicitly stated to the contrary. Moreover, the terms channel and microchannel will be used synonymously and interchangeably and refer generally to channels having dimensions on the order of about 5–100 μm wide and 5–100 μm deep Consider now fluid flow through the system illustrated in FIG. 5 during various phases of operation of the system. Initially, a sample to be analyzed is introduced into first reservoir 141 and subsequently caused to flow (generally by electroosmotic flow or pressure-driven flow) from first reservoir 141 through sample channel 110 to second reservoir 142. At some later time, a portion of the sample flowing in sample channel 140 is injected into separation channel 120 and is caused to traverse the length of separation channel 120 by flowing a fluid such as a running buffer from first reservoir 115 through the separation channel. During passage through the separation channel to second reservoir 125 the sample is separated into its components.

The auxiliary flow channels 130 are designed such that there is a much smaller fluid flow through these channels due to the smaller cross-sectional area of the auxiliary channels. Thus, during the injection mode, i. e., when a sample to be analyzed is injected into separation channel 120, auxiliary channels 130 have minimal impact on the system. However, during the separation mode the gradient (electric field or pressure) and thus the linear flow velocity is comparable in all three channels. Fluid will flow from first reservoir 115 to second reservoir 125 through all three paths. As shown by the fluid flow lines in FIG. 5, the flow along the alternate pathway provided by the auxiliary channels forces unwanted sample-filled liquid away from the intersection region eliminating the problem of sample siphoning.

Figure 6:
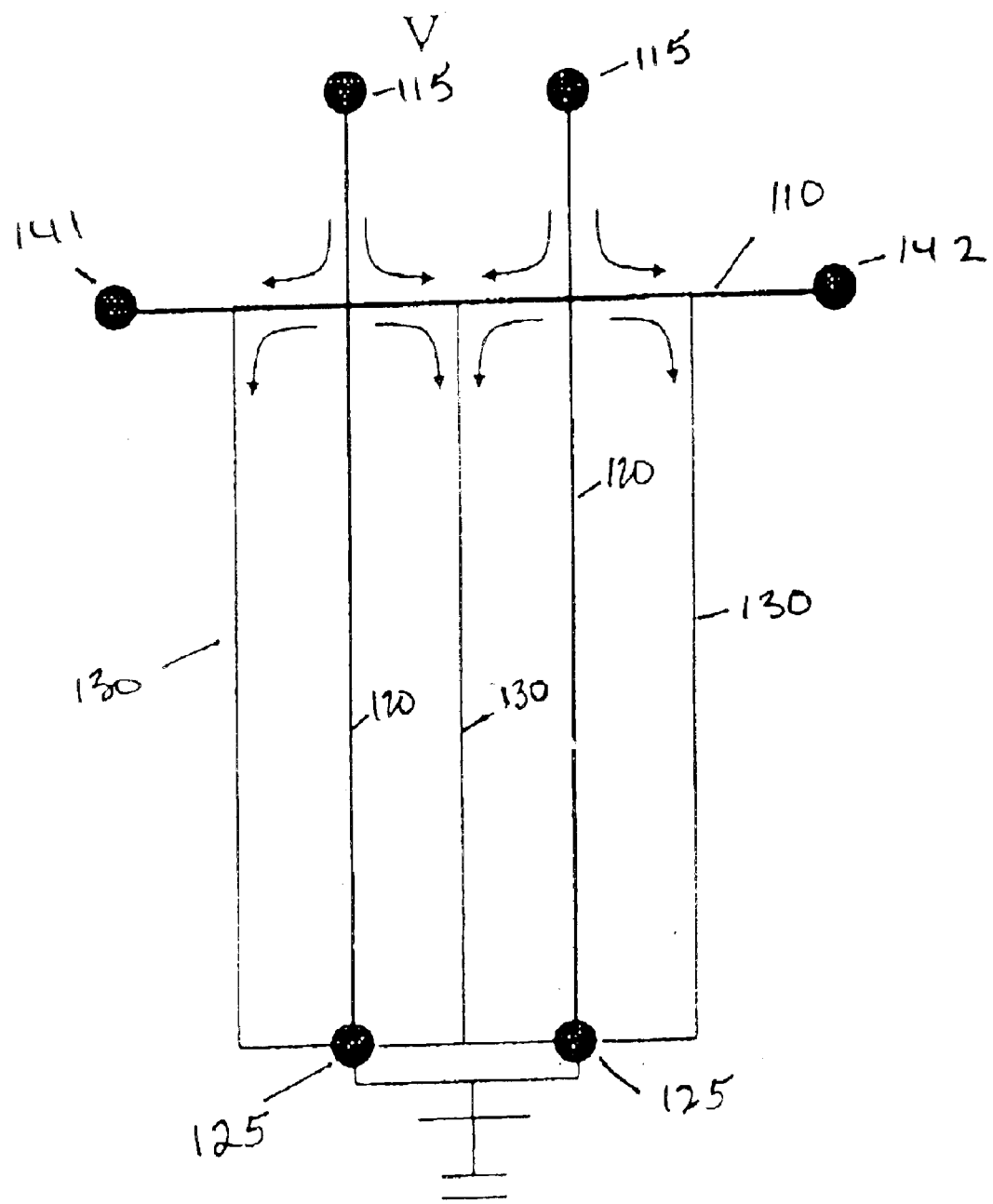
FIG. 6 shows a two-channel embodiment of the invention.

Another embodiment of the invention is passive injection control for a multi-channel system, as illustrated in FIG. 6 for a two-channel configuration. As before, each separation channel 120 is provided with auxiliary flow channels 130. It should be noted in this embodiment that the center auxiliary flow channel 130 is common to both separation channels. By providing the auxiliary channel configuration described herein the present invention is capable of removing sample volume not only from outside the two separation channels but also any sample trapped between the separation channels, a capability not present in prior art sample injection methods.

Additionally, as will be appreciated by those skilled in the art, separations in parallel channels can require buffer solutions having different compositions. In these cases, the buffer solutions can have different electrochemical properties and thus, an electroosmotic force can arise between parallel channels which can cause the characteristic plug-like electroosmotic flow to be distorted. Due to a conservation of material, the system automatically matches volumetric flow by automatically adding a parabolic flow component into the fluid flow. By incorporating the auxiliary flow channels discussed above, flow distortion can be substantially eliminated, thereby improving sample analysis.

By removing trapped sample between parallel channels, such as would be encountered in prior art microfluidic analysis systems, the present invention provides for decreased analysis time and a reduction in sample volume. This is a consequence of the fact that in order to remove trapped sample between channels a more complex injection sequence would need to be employed, to wit:

Flow the sample into the injection volume;
Sweep the sample from the injection volume into the separation column;
Sweep clean buffer solution from a second reservoir through the sample introduction channel to remove trapped sample; and
Complete the sample analysis.

In the aforementioned scheme for removing trapped sample, in addition to needing additional reservoirs and optimized voltage switching times, it is necessary to recognize that the separation efficiency must be decreased in this mode because of the latent time during which the sample plug remains idle in the separation column during the sweep step.

In the design of systems employing the passive injection control described above, consideration must be given to the relative flow rates through the sample and auxiliary channels. The flow rate through the auxiliary channels should be sufficient to move sample away from the injection region in a timely fashion but not so rapidly that running buffer is unnecessarily wasted or distortions are caused to take place in the fluid flow pattern. It is desirable that the sum of the volumetric fluid flow rates through the auxiliary channels be less than that through the separation channels. Since the driving potential across the separations and auxiliary channels as well as the properties of the fluid are the same, the flow rate through the channels scales as A/L, thus one factor that can be considered in proportioning fluid flow rate through the separation channel and associated auxiliary channels is the cross sectional area of the channel (A) divided by the length (L) of the channel. It has been found that successful application of the invention can be obtained if the ratio of flow rates through the sample channel and the auxiliary channels is ≈10:1. Thus, the rate of fluid flow through the auxiliary channels can be controlled by changes in the cross-sectional area of the channels or their length, such as by configuring the auxiliary channels in a spiral or serpentine pattern. It should be noted that this ratio is for the sum of the flow rates through the various channels, which means that individual auxiliary channels can have different volumetric flow rates providing the sum of flow rates through the plurality of auxiliary channels falls within the proper value.

A second approach to adjusting fluid flow rate is to fill the auxiliary channels with an appropriate medium, that can be a particulate or porous medium, to provide a resistance to fluid flow such that the flow rate through the auxiliary channels is less than that through the sample channel and preferably about 10% of that of the sample channel. The medium can be, but not limited to, silica-based chromatographic particles, porous polymeric materials, or etched structures.

An obvious variation of the methods for adjusting relative flow rates discussed above is to combine them. Thus, control of fluid flow rate through the auxiliary channels can be by cross-sectional area of the channel, length, incorporation of suitable porous media in the channel itself, or combinations thereof.

The foregoing is intended to be illustrative of the present invention and is provided for purposes of clarity and understanding of the principles of this invention. Many other embodiments and modifications can be made by those of skill in the art without departing from the spirit and scope of the invention as defined in the following claims.

We claim:

1. An apparatus for passive control of sample transport through microchannels, comprising:
   a separation channel having an inlet end and an outlet end, wherein said separation channel is provided with a first reservoir in fluid communication with the inlet end and a second reservoir in fluid communication with the outlet end;
   a sample channel having an inlet end and an outlet end intersecting and in fluid communication with said separation channel, wherein said sample channel is provided with a first reservoir in fluid communication with the inlet end and a second reservoir in fluid communication with the outlet end; and
   at least two auxiliary flow channels, each having an inlet and outlet end, disposed on both sides of said separation channel, wherein the inlet ends of said auxiliary flow channels are in fluid communication with said sample channel and the outlet ends of said auxiliary flow channels are joined to said separation channel, and wherein the sum of the rates of fluid flow through said auxiliary flow channels is less than that through said separation channel.

2. The apparatus of claim 1, wherein the sum of the rate of fluid flow through said auxiliary flow channels is about 10% of that through said separation channel.

3. The apparatus of claim 1, wherein said auxiliary channels are disposed in parallel alignment with and equidistant from said separation channel.

4. The apparatus of claim 1, wherein said auxiliary channels are spaced from the separation channel a distance of at least about 5 hydraulic diameters of said sample channel.

5. The apparatus of claim 1, wherein said auxiliary flow channels are configured in a spiral or a serpentine pattern.

6. The apparatus of claim 1, wherein said auxiliary channels have a particulate or porous material disposed therein.

7. The apparatus of claim 6, wherein the material is silica-based particles, porous polymeric materials, or etched structures.

8. The apparatus of claim 1, wherein the cross-sectional area of said auxiliary flow channels is the same or different.

9. The apparatus of claim 1, wherein the length of said auxiliary flow channels is the same or different.

10. The apparatus of claim 1, wherein said separation channel comprises a plurality of separation channels.

11. An apparatus for chromatographic analysis, comprising:
   a substrate fabricated to define a microchannel system disposed thereon, the microchannel system comprising;
   a separation channel having first and second reservoirs in fluid communication with said separation channel,
   a sample channel having first and second reservoirs in fluid communication with said sample channel, and
   auxiliary flow channels disposed on both sides of said separation channel, each auxiliary flow channel having an inlet and outlet end, wherein the inlet ends of said auxiliary channels are in fluid communication with said sample channel and the outlet ends of said auxiliary channels are joined to said separation channel, and wherein the rate of fluid flow through said auxiliary channels is less than that through said separation channel.

12. The apparatus of claim 11, wherein the rate of fluid flow through said auxiliary channels is about 10% of that through said separation channel.

13. The apparatus of claim 11, wherein said auxiliary channels are disposed in parallel alignment with and equidistant from said separation channel.

14. The apparatus of claim 11, wherein said auxiliary channels are spaced from the separation channel a distance of at least about 5 hydraulic diameters of said sample channel.

15. The apparatus of claim 11, wherein said auxiliary flow channels are configured in a spiral or a serpentine pattern.

16. The apparatus of claim 11, wherein said auxiliary channels have a particulate or porous material disposed therein.

17. The apparatus of claim 16, wherein the material is silica-based particles, porous polymeric materials, or etched structures.

18. The apparatus of claim 11, wherein the cross-sectional area of said auxiliary flow channels is the same or different.

19. The apparatus of claim 11, wherein the length of said auxiliary flow channels is the same or different.

20. The apparatus of claim 11, wherein said separation channel comprises a plurality of separation channels.

* * * * *